US008653291B2

(12) United States Patent
Delapierre et al.

(10) Patent No.: US 8,653,291 B2
(45) Date of Patent: Feb. 18, 2014

(54) METHOD FOR SURFACE FUNCTIONALIZATION BY DISUBSTITUTED ALKYNES

(75) Inventors: Guillaume Delapierre, Vif (FR); Regis Barattin, Grenoble (FR); Aude Bernardin, Lailly-en-Val (FR); Isabelle Texier-Nogues, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 197 days.

(21) Appl. No.: 13/257,398

(22) PCT Filed: Mar. 16, 2010

(86) PCT No.: PCT/FR2010/000222
§ 371 (c)(1),
(2), (4) Date: Nov. 1, 2011

(87) PCT Pub. No.: WO2010/106246
PCT Pub. Date: Sep. 23, 2010

(65) Prior Publication Data
US 2012/0095247 A1 Apr. 19, 2012

(30) Foreign Application Priority Data
Mar. 18, 2009 (FR) ...................................... 09 01255

(51) Int. Cl.
*C07F 17/00* (2006.01)
*C07F 7/00* (2006.01)

(52) U.S. Cl.
USPC ............................................... 556/11; 556/87

(58) Field of Classification Search
USPC ...................................................... 556/11, 87
See application file for complete search history.

(56) References Cited

U.S. PATENT DOCUMENTS
2009/0270590 A1   10/2009  Jun et al.

FOREIGN PATENT DOCUMENTS
WO   2007 024055   3/2007

OTHER PUBLICATIONS
International Search Report Issued May 25, 2010 in PCT/FR10/000222 filed Mar. 16, 2010.

*Primary Examiner* — Porfirio Nazario Gonzalez
(74) *Attorney, Agent, or Firm* — Oblon, Spivak, McClelland, Maier & Neustadt, L.L.P.

(57) ABSTRACT

The invention relates to the use of disubstituted alkynes for the functionalisation of the surface of a substrate consisting of a semi-conductor material, with molecules of interest. According to the invention, a compound of formula $A\text{-}(E1)_{n1}\text{-}F1$ is used, wherein A is a linear or cyclic disubstituted alkyne, E1 is an alkyl chain and n2 is 0 or 1, and F1 is a reactive group that can react with the reactive group F2 of a compound of formula $F2\text{-}(E2)_{n2}\text{-}X$ wherein E2 is an alkyl chain and X is a group having properties of interest. The invention is especially applicable to the field of molecular biology or biotechnology.

15 Claims, No Drawings

METHOD FOR SURFACE FUNCTIONALIZATION BY DISUBSTITUTED ALKYNES

The invention relates to the use of disubstituted alkynes for the functionalization of the surface of a substrate made of a semiconducting material with molecules of interest and to a process for the functionalization of the surface of a substrate made of a semiconducting material with molecules of interest.

The functionalization of the surface of a support made of a semiconducting material, in particular made of silicon or germanium or their alloys, such as SiC, SiGe, and the like, is the subject of many research studies, in particular in the field of miniaturized electronic components and in the field of molecular biology.

In the field of molecular biology or biotechnologies, the functionalization of the surface of the substrate made of a semiconducting material is carried out with biological molecules, such as DNA molecules, peptides, proteins, and the like, for applications in the field of medical research, medical diagnostics, of the monitoring of the environment, or of civilian and military safety, and the like.

In the field of molecular electronics, the functionalization of a substrate made of a semiconducting material by redox molecules is used in particular for memory applications.

In this case, the various available redox states of the redox molecules are used to store information on the surface, by varying the voltage applied to the system: by applying a voltage corresponding to the oxidation potential of the grafted molecules, the surface becomes charged: the writing of the data is thus carried out; by returning to the initial state (reduction), the surface again becomes neutral, this corresponds to the erasing of the data.

Various methods for the functionalization of the surface of a substrate made of germanium or of silicon have been provided, in particular in J.M. Buriak, Chem. Rev., 2002, 1271-1308.

The most commonly used reactions are:
The reaction of monofunctionalized terminal alkenes and alkynes by thermal or photochemical activation. To date, only the reactions of mono- or disubstituted alkenes and of monosubstituted alkynes have been envisaged. Thus, R. Terborg et al., Phys. Rev. B, 2000, 16697-16703, and Morikawa et al., Phys. Rev. B, 2001, 63, 33405, have carried out theoretical studies on the absorption of acetylene on silicon surfaces.

The reaction of diazonium salts or of metal anions of formula RMgX or RLi by electrical activation. This reaction has been described in particular by J. Tour et al., JACS, 2004, 370-378.

Thus, several methods for the functionalization of surfaces make it possible today to graft organic molecules to nonoxidized surfaces of silicon or of germanium.

However, these reactions need to be activated in order to take place. The activations can be thermal, photochemical, catalytic or electrical activations.

An aim of the invention is to make it possible to functionalize the surface of a substrate made of silicon or of germanium by using less activation energy than with the mono- or disubstituted alkenes and than with the monosubstituted alkynes used in the prior art in this way or by the reaction of the diazonium salts or of metal anions.

To this end, the invention provides for the use of a compound of following formula I:

$$A\text{-}(E1)_{n1}\text{-}F1 \qquad \text{Formula I}$$

in which:
A is chosen from:
1) an alkyne of formula:

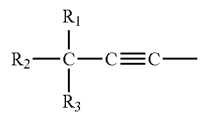

in which:
$R_1$, $R_2$ and $R_3$ are identical or different and are chosen, independently of one another, from the group formed by a hydrogen atom; a halogen atom; an —OH group; an —$NH_2$ group; an —SH group and a saturated, linear or branched, $C_1$ to $C_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms; and
2) an 8- to 12-membered cycloalkyne or hetero-cycloalkyne which is optionally substituted by an $R_1$ group as defined above, E1 is a saturated or unsaturated, linear or branched, $C_1$ to $C_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms, n1=0 or 1, and F1 is a reactive group capable of reacting with a reactive group F2 of a molecule of interest of following formula II:

$$F2\text{-}(E2)_{n2}\text{-}X \qquad \text{Formula II}$$

in which:
F2 is a reactive group capable of reacting with the reactive group F1 of the compound of formula I,
E2 is a saturated or unsaturated, linear or branched, $C_1$ to $C_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms,
n2=0 or 1, and
X is a group having properties of interest, for the functionalization with molecules of interest of the surface of a substrate made of a semiconducting material.

Preferably, the semiconducting material of the substrate is chosen from silicon, germanium and alloys and mixtures of these.

Most preferably, in the formula I, E1 is a saturated, linear or branched, $C_1$ to $C_5$ alkyl chain which can comprise at least one heteroatom.

Preferably, in A, $R_1$ and $R_2$ and $R_3$, when present, are identical or different and are chosen, independently of one another, from the group formed by a hydrogen atom; a halogen atom and a saturated, linear or branched, $C_1$ to $C_{30}$ alkyl chain which optionally comprises heteroatoms and/or aryl groups and/or amine groups and/or which is optionally substituted by halogen atoms.

More preferably, in A, $R_1$ is a linear or branched $C_1$ to $C_5$ alkyl chain which can comprise at least one heteroatom and $R_2$ and $R_3$, when present, are H.

In a first preferred embodiment of the use of the invention, in the formula I, A is an unsubstituted cyclooctyne.

Still preferably, F1 and F2 are chosen from a carboxyl group, a radical entity, a hydroxyl group, an alcohol group, an amine group, an ester group, an aldehyde group, a hydrazide group, a ketone group, an epoxy group, an isocyanate group, a maleimide group, a thiol group and a hydroxylamine group.

In a preferred embodiment of the use of the invention, in the compound of formula I:
in A, $R_1$ and $R_2$ and $R_3$, when present, are H,
n1 has the value 0,
F1 is a —COOH radical, and
F2 is an —$NH_2$ radical.

In another preferred embodiment of the use of the invention, in the formula I:
in A, $R_1$ and $R_2$ and $R_3$, when present, are H,
n2=1,
E1 is a —$C_6H_{12}$— chain,
F1 is a —COOH radical, and
F2 is an —$NH_2$ radical.

In a preferred alternative form of the use of the invention, in the formula I:
A is an unsubstituted cyclooctyne,
n1=1,
E1 is an —O—$CH_2$— chain,
F1 is a —COOH radical, and
F2 is an —$NH_2$ radical.

Preferably, in all the embodiments and alternative forms of the use of the invention, in the formula II, E2 is a —$(CH_2)_2$—O—$CH_2$— chain.

In addition, in all the embodiments and alternative forms of the use of the invention, in the formula II, X is chosen from the group consisting of a porphyrin molecule, an anthracene molecule, a naphthalene molecule, a fullerene molecule, a polyoxometalate molecule and a ferrocene group. Most preferably, X is a ferrocene group.

The invention also provides a process for the functionalization of the surface of a substrate made of a semiconducting material, characterized in that it comprises the following stages:

a) reaction of the reactive group F1 of a compound of formula I of following formula:

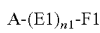 Formula I in which:
A is chosen from:
1) an alkyne of formula:

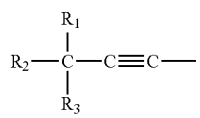

in which:
$R_1$, $R_2$ and $R_3$ are identical or different and are chosen, independently of one another, from the group formed by a hydrogen atom; a halogen atom; an —OH group; an —$NH_2$ group; an —SH group and a saturated, linear or branched, $C_1$ to $C_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms; and
2) an 8- to 12-membered cycloalkyne or heterocloalkyne which is optionally substituted by an $R_1$ group as defined above, E1 is a saturated or unsaturated, linear or branched, $C_1$ to $C_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms,
n1=0 or 1,
with a reactive group F2 of a molecule of interest of following formula II:

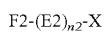 Formula II in which:
F2 is a reactive group capable of reacting with the reactive group F1 of the compound of formula I,
E2 is a saturated or unsaturated, linear or branched, $C_1$ to $C_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms,
n2=0 or 1, and
X is a group having properties of interest, for the functionalization with molecules of interest of the surface of a substrate made of a semiconducting material, and
b) reaction of the triple bond of the compound of formula I with the semiconducting material.

In a first alternative form of the process of the invention, stage b) is carried out before stage a).

In this case, optionally, the process of the invention additionally comprises:
a stage a1) of protection of the reactive group F1, before carrying out stage a), and
a stage b1) of deprotection of the reactive group F1, before carrying out stage b).

In a second alternative form of the process of the invention, stage a) is carried out before stage b).

In all the alternative forms of the process of the invention, the semiconducting material of the substrate is preferably chosen from silicon, germanium and their alloys and mixtures.

Most preferably, in the formula I, E1 is a saturated, linear or branched, $C_1$ to $C_5$ alkyl chain which can comprise at least one heteroatom.

Preferably, in A, $R_1$ and $R_2$ and $R_3$, when present, are identical or different and are chosen, independently of one another, from the group formed by a hydrogen atom; a halogen atom and a saturated, linear or branched, $C_1$ to $C_{30}$ alkyl chain which optionally comprises heteroatoms and/or aryl groups and/or amine groups and/or which is optionally substituted by halogen atoms.

More preferably, in A, $R_1$ is a linear or branched $C_1$ to $C_5$ alkyl chain which can comprise at least one heteroatom and $R_2$ and $R_3$, when present, are H.

Preferably, in the process of the invention, in the formula I, A is an unsubstituted cyclooctyne.

Still preferably, in the process of the invention, F1 and F2 are chosen from the group consisting of a carboxyl group, a radical entity, a hydroxyl group, an alcohol group, an amine group, an ester group, an aldehyde group, a hydrazide group, a ketone group, an epoxy group, an isocyanate group, a maleimide group and a thiol group.

In a first embodiment of the process of the invention, in the formula I:
in A, $R_1$ and $R_2$ and $R_3$, when present, are H,
n1 has the value 0,
F1 is a —COOH radical, and
F2 is an —$NH_2$ radical.

In a second embodiment of the process of the invention, in the formula I:

in A, $R_1$ and $R_2$ and $R_3$, when present, are H, $n1=1$,

E1 is a —$C_6H_{12}$— chain,

F1 is a —COOH radical, and

F2 is an —$NH_2$ radical.

In a third embodiment of the process of the invention, in the formula I:

A is an unsubstituted cyclooctyne, $n1=1$,

E1 is an —O—$CH_2$— chain,

F1 is a —COOH radical, and

F2 is an —$NH_2$ radical.

In all the alternative forms and embodiments of the process of the invention, preferably in the formula II, E2 is a —$(CH_2)_2$—O—$CH_2$— chain.

Also preferably, in the formula II, X is chosen from the group consisting of a porphyrin molecule, an anthracene molecule, a naphthalene molecule, a fullerene molecule, a polyoxometalate molecule and a ferrocene group. Most preferably, X is a ferrocene group.

A better understanding of the invention will be obtained and other characteristics and advantages of the invention will become more clearly apparent on reading the explanatory description which follows.

The invention is based on the use of disubstituted alkynes which have an increased reactivity with substrates made of semiconducting materials, in comparison with monosubstituted or disubstituted alkenes and in comparison with monosubstituted alkynes.

In the invention, this increase in reactivity of the disubstituted alkynes is used to functionalize the substrate by reaction of the triple bond of the disubstituted alkyne as defined in the invention with reactive groups present on the substrate itself.

The disubstituted alkynes used in the invention are furthermore stable, which makes it possible to functionalize the surfaces of a substrate made of a semiconducting material in a lasting fashion over time, which is not the case, for example, with the diazonium salts, which are highly reactive and tend to decompose fairly rapidly.

In the invention, the following terms have the following meanings:

molecule of interest or group of interest: any molecule exhibiting a functionality of use in reactions on a solid support, for example synthetic reactions or reactions for direct or indirect detection. This molecule of interest can, for example, without this list being limiting, be a biomolecule, such as a protein (in particular an enzyme), an amino acid, a peptide, an antibody, an antigen, which may or may not be modified; a glycopeptide, a lipid, a steroid, a glycolipid, a sugar, a polysaccharide, which may or may not be modified; a DNA or RNA molecule, an oligonucleotide, which may or may not be modified; a molecule capable of generating, directly or indirectly, a signal, or else a complex, multifunctional molecule; and the like. Advantageously, this molecule of interest constitutes one of the members of an affinity pair; it can, for example, be biotin, or a potentially antigenic peptide, a hapten, and the like, disubstituted alkyne: compound of formula R—C≡C—R' in which R and R' are other than H. In contrast, a monosubstituted alkyne is a compound of formula H—C≡C—R'. The R' group can be any group and in particular the reactive group F1 as defined in the invention, molecule of interest: molecule comprising a group having specific properties and which it is desired "to graft" to the surface of a support made of a semiconducting material, alkyne carbon: carbon bonded to a triple bond, "X"-membered cycloalkyne: ring comprising "X" carbon-carbon bonds forming a ring, one of these bonds being a triple bond, heterocycloalkyne: cycloalkyne as defined above, in which one or more carbon atoms are replaced by a heteroatom, such as O, N or S, silicon alloy: material comprising silicon as an alloy with another compound, such as, for example, silicon carbide, and the like, germanium alloy: material comprising germanium as an alloy with another compound, such as, for example, germanium carbide (GeC), mixture of silicon and germanium: material composed of silicon and germanium, in all proportions, radical entity: chemical entity having one or more unpaired electrons.

The disubstituted alkyne used in the invention has the following formula I:

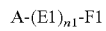     Formula I in which:

A is either an alkyne of formula:

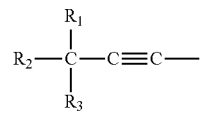

in which:

$R_1$, $R_2$ and $R_3$ are identical or different and are chosen, independently of one another, from the group formed by a hydrogen atom; a halogen atom; an —OH group; an —$NH_2$ group; an —SH group and a saturated, linear or branched, $C_1$ to $C_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms;

or an 8 to 12-membered cycloalkyne or heterocyclo-alkyne which is optionally substituted by an $R_1$ group as defined for the alkyne of formula:

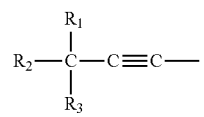

E1 is a saturated or unsaturated, linear or branched, $C_1$ to $C_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms, $n1=0$ or 1, and F1 is a reactive group capable of reacting with a reactive group F2 of a molecule of interest of following formula II:

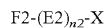     Formula II in which:
- F2 is a reactive group capable of reacting with the reactive group F1 of the compound of formula I,
- E2 is a saturated or unsaturated, linear or branched, $C_1$ to $C_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms,
- n2=0 or 1, and
- X is a group having properties of interest, for the functionalization with molecules of interest of the surface of a substrate made of a semiconducting material.

It is thus seen that the reactive groups F1 and F2 are chosen as a function of one another.

They are preferably chosen from the group consisting of a carboxyl group, a radical entity, a hydroxyl group, an alcohol group, an amine group, a hydroxylamine group, an ester group, an aldehyde group, a hydrazide group, a ketone group, an epoxy group, an isocyanate group, a maleimide group or a thiol group.

More specifically:
- when F1 is a carboxyl group, F2 is preferably an amine or alcohol group,
- when F1 is a radical entity, F2 is preferably another radical entity,
- when F1 is a hydroxyl group or an alcohol group, F2 is preferably a carboxyl or isocyanate group,
- when F1 is an amine group, F2 is preferably an ester or aldehyde group,
- when F1 is an ester group, F2 is preferably an amine or alcohol group,
- when F1 is an aldehyde group, F2 is preferably a hydrazide or amine or hydroxylamine group,
- when F1 is a hydrazide group, F2 is preferably an aldehyde group,
- when F1 is a ketone group, F2 is preferably an alcohol group; more preferably F2 is a group comprising 2 alcohol groups for a reaction with F1 by acetalization,
- when F1 is an epoxy group, F2 is preferably an amine or alcohol or thiol group,
- when F1 is an isocyanate group, F2 is preferably a hydroxyl group,
- when F1 is a maleimide group, F2 is preferably chosen from a thiol group, an amine group or a diene group,
- when F1 is a thiol group, F2 is chosen from a maleimide or thiol or epoxide group, and
- when F1 is a hydroxylamine group, F2 is chosen from an aldehyde or ketone group.

With regard to E1, it is preferably a saturated, linear or branched, $C_1$ to $C_5$ alkyl chain which can comprise at least one heteroatom.

Preferably, $R_1$ and $R_2$ and $R_3$, when $R_2$ and $R_3$ are present, that is to say, are identical or different and are chosen, independently of one another, from the group formed by a hydrogen atom; a halogen atom and a saturated, linear or branched, $C_1$ to $C_{30}$ alkyl chain which optionally comprises heteroatoms and/or aryl groups and/or amine groups and/or which is optionally substituted by halogen atoms.

The terms "in A, $R_1$ and $R_2$ and $R_3$, when present" encompass the case in which A is a linear alkyne substituted by $R_1$, $R_2$ and $R_3$ and the case in which A is a (hetero)cycloalkyne substituted solely by $R_1$.

More preferably, $R_1$ is a linear or branched $C_1$ to $C_5$ alkyl chain which can comprise at least one heteroatom, and $R_2$ and $R_3$ are H.

The disubstituted alkyne used in the invention and in the functionalization process of the invention can be an alkyne comprising a linear chain, in which case it has the formula:

$$R_2-\underset{\underset{R_3}{|}}{\overset{\overset{R_1}{|}}{C}}-C\equiv C-$$

where $R_1$, $R_2$ and $R_3$ are as defined above.

Most preferably, in this formula, $R_1$ is a linear or branched $C_1$ to $C_5$ alkyl which can comprise at least one heteroatom, such as O, N or S, and $R_2$ and $R_3$ are H.

In this embodiment of the use and of the functionalization process of the invention, in a first alternative form, n1 is equal to zero and the disubstituted alkyne used in the invention has the formula:

$$R_2-\underset{\underset{R_3}{|}}{\overset{\overset{R_1}{|}}{C}}-C\equiv C-F1$$

In a second preferred alternative form of this embodiment, n1 is equal to 1 and E1 is a $-C_6H_{12}-$ chain.

In this second preferred alternative form, the disubstituted alkyne used in the invention has the formula:

$$R_2-\underset{\underset{R_3}{|}}{\overset{\overset{R_1}{|}}{C}}-C\equiv C-C_6H_{12}-F1$$

In these two alternative forms of the invention, preferably, $R_1$, $R_2$ and $R_3$ are H and F1 is a $-COOH$ radical.

As F1 is a group capable of reacting with a reactive group F2 of a molecule of interest, where F1 is a $-COOH$ radical, preferably, the reactive group denoted F2 of the molecule of interest is preferably an $-NH_2$ radical.

However, in a very particularly preferred embodiment of the functionalization process of the invention and of the use of the invention, the disubstituted alkyne is a cyclic alkyne or heteroalkyne which is optionally substituted.

In this case, preferably, the disubstituted alkyne used in the invention has the following general formula:

$$yCH_2-\text{cyclooctyne}-(E_1)_{\overline{n_1}}-F_1$$

in which:
- y is an integer between 1 and 5 inclusive, and
- E1, n1 and F1 are as defined for the compounds of formula I.

In a very particularly preferred alternative form of the invention, the cyclic disubstituted alkyne is a cyclooctyne.

This is because the cyclooctyne group is a particularly stable cyclic group.

Still when the disubstituted alkyne is a cycloalkyne, preferably, E1 is an —O—CH$_2$— chain and F1 is a —COOH radical, in which case, preferably, the F2 group of the molecule of interest is an —NH$_2$ radical.

The substrate made of a semiconducting material, this being the case in all the embodiments and all the alternative forms of the process and of the use of the invention, is preferably made of nonoxidized silicon, of nonoxidized germanium or of alloys or mixtures of these.

With regard to the molecule of interest, it has the following formula II:

F2-(E2)$_{n2}$-X in which:
F2 is a group capable of reacting with the reactive group F1 of the disubstituted alkyne used in the invention,
E2 is a saturated or unsaturated, linear or branched, C$_1$ to C$_{30}$ alkyl chain which optionally comprises heteroatoms and/or aryl groups and/or amine groups and/or ester groups and/or hydroxylamine groups and/or oxime groups and/or amide groups and/or which is optionally substituted by halogen atoms. Preferably, E2 is a linear C1 to C5 alkyl chain which can comprise a heteroatom, such as oxygen, nitrogen or sulfur.
Preferably, the heteroatom is an oxygen.
n2 has a value 0 or 1, and
X is a group having properties of interest.
Preferably, in the formula II, the reactive group F2 is an —NH$_2$ radical. With regard to the group E2, in a preferred embodiment of the invention, it is a
(CH$_2$)$_2$—O—CH$_2$— chain.

With regard to the group X having the properties of interest, it is chosen from the group consisting of a porphyrin molecule, an anthracene molecule, a naphthalene molecule, a fullerene molecule, a polyoxometalate molecule and a ferrocene group.

In a particularly preferred embodiment of the use of the process of the invention, it is a ferrocene group.

In the process and the use of the invention, preferably, the E1 group and/or E2 group have at least four linking members, in order to reduce the steric hindrance at the surface of the substrate made of a semiconducting material to the group of interest X.

The process of the invention comprises a) the reaction of the group F1 of the compound of formula I with the group F2 of the molecule of interest of formula II and b) the reaction of the triple bond of the disubstituted alkyne of formula I of the invention with the surface of the substrate to be functionalized.

With regard to the substrate, it is preferably made of a semiconducting material chosen from silicon, germanium and the mixtures of these.

In the case of a substrate made of silicon or based on silicon, that is to say comprising at least 20 mol % of silicon, with respect to the total number of moles of the material constituting the substrate, the reaction b) takes place by a hydrosilylation reaction of the triple bond of the disubstituted alkyne of formula I with the hydrogens bonded to the silicon surface the substrate.

In the case of a substrate made of germanium or of a substrate based on germanium, here again it concerns a reaction between the triple bond of the disubstituted alkyne of formula I used in the invention and the hydrogens bonded to the germanium surface of the substrate.

It is possible, of course, as will be clearly apparent to a person skilled in the art, to first carry out the reaction between the triple bond of the disubstituted alkyne used in the invention and the surface of the substrate made of semiconducting material as defined above and then to carry out the reaction of the reactive group F1 with the reactive group F2 of the molecule of interest with which it is desired to functionalize the surface of the substrate used in the invention or first to bond the molecule of interest by reaction of the group F1 of the disubstituted alkyne of formula I with the reactive group F2 of the molecule of interest and only subsequently to carry out the "grafting" of the compound obtained to the surface of the substrate, that is to say to carry out the reaction of the triple bond of the disubstituted alkyne used in the invention with the surface of the substrate used in the invention.

When the reaction between the triple bond of the disubstituted alkyne in the invention is carried out first, it may be necessary to protect the reactive group F1 before this reaction and then to deprotect the group F1 in order to react it with the group F2.

In order to make the invention better understood, several embodiments thereof will now be described as purely illustrative and nonlimiting examples.

In all the examples which follow, use has been made of a substrate made of nonoxidized silicon with a thickness of 500 µm and, as group of interest, a ferrocene group which makes it possible to easily confirm, by cyclic voltammetry, that the use of disubstituted alkynes according to the invention makes it possible to functionalize the surface of a substrate with ferrocene groups, while requiring less activation energy (lower grafting temperature) than with the alkynes or alkenes of the prior art.

REFERENCE EXAMPLE 1

A monosubstituted alkyne according to the prior art, ethynylferrocene of following formula I-E:

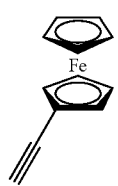

Formula I-E was grafted to the silicon substrate at temperatures of 100° C., 130° C. and 180° C.

This grafting was carried out in the following way:

A silicon surface, hydrogenated beforehand by treatment with 1% HF, is introduced into a 1 mM solution of the reference alkyne of formula I-E in mesitylene. The reaction medium is heated (100° C./130° C./180° C.) under an argon atmosphere for 2 h. After cooling to ambient temperature, the surface is washed and subjected to ultrasound in dichloromethane and dried under argon.

The results obtained are as follows:
At 180° C. (reference temperature);
The compound of formula I-E gives an electrochemical signature indicating that it is indeed grafted to the surface.
The drift of the baseline is slightly more pronounced, indicating that a small amount of surface oxide is formed. This is because there is always a competition between the grafting reaction and the reaction for formation of oxide (due to the traces of oxygen and of water in the medium). The more reactive the compound to be grafted, the less this oxide is formed.

At 130° C.:

This temperature is generally too low for monosubstituted alkynes to react.

This is observed with regard to the compound of formula I-E, the redox activity of which is visible but very strongly masked by a strong oxidation of the substrate, indicating that the ferrocene has only partially reacted.

At 100° C.:

No reactivity of the compound of formula I-E.

Disubstituted alkynes according to the invention were then used to carry out the same type of grafting.

The results are as follows:

EXAMPLE 2

The disubstituted alkyne according to the invention used in this example is cyclooct-1-yne-3-glycolic acid of following formula:

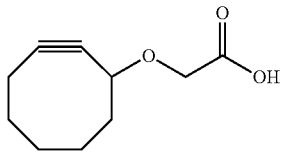 [SMILES: O=C(O)COC1C#CCCCCC1]

The molecule of interest is a molecule having a ferrocene group of formula:

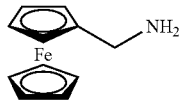

The following procedure was carried out:

1—Synthesis of 8,8-dibromobicyclo[5.1.0]octane[5-9]

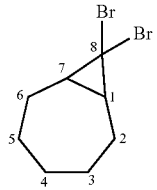

3.65 g of cycloheptene (i.e., 38 mmol), then 8.52 g of t-BuOK (i.e., 76 mmol, 2 eq.) and 9 ml of predistilled pentane are introduced into a dry round-bottomed flask under argon. The cream yellow solution is vigorously stirred and placed in an ice/salt bath. 4.9 ml of bromoform (i.e., 57 mmol, 1.5 eq.) are then added dropwise. During the addition of the first drops, a fairly violent evolution of gas is observed and then, as the addition proceeds, the solution becomes ochre brown. During the addition, approximately 5 ml of pentane were added in order to make possible correct stirring of the solution. Once the addition is complete, the mixture is allowed to return to ambient temperature overnight, under argon and with vigorous stirring.

Approximately 50 ml of water are subsequently added and the pH is neutralized with 1M HCl. The organic and aqueous phases are separated; the aqueous phase is extracted with 3×20 ml of pentane and the pentane phase is washed with 3×20 ml of water. The organic phase is subsequently dried over $MgSO_4$ and the solvent is evaporated under vacuum. An orangey yellow oil is obtained with a weight w=10.814 g.

The product is subsequently purified by simple filtration through silica with cyclohexane/AcOEt 5% as eluent. A colorless oil with a total weight of 9.100 g is obtained after purification, i.e. with a yield of 90% (litt. 52-65% for 9,9-dibromobicyclo[6.1.0]nonane).

$R_f$(cyclohexane 95/AcOEt 5)=0.85;

$^1$H NMR ($CDCl_3$, 200 MHz): δ (ppm) 1.05-1.22 (m, 3H); 1.34 (qq, J=1 and 7.5 Hz, 2H); 1.68 (ddd, J=1.5, 4 and 10.5 Hz, 2H); 1.76-1.92 (m, 3H): 2.23 (dtq, J=14, 6 and 1 Hz, 2H);

$^{13}$C NMR ($CDCl_3$, 50 MHz): δ (ppm) 40.7 ($C_8$ quat.); 34.8 (2, $C_{1,7}$); 32.2 ($C_4$); 28.9 (2, $C_{2,6}$); 27.9 (2, $C_{3,5}$);

Mass: $ESI^+$ m/z $[M+H_2O+H]^+$=284.4 for 284.9; $[M+HBr+Na]^+$=368.5 for 396.93

IR: υ ($cm^{-1}$) 2921 $υ_{CH}$; 2853 $υ_{CH2}$; 1457 $δ_{CH}$; 1354 $δ_{tertiary\ CH}$; 735 $υ_{CBr}$.

2—Synthesis of methyl 2-bromocyclooctene-3-glycolate

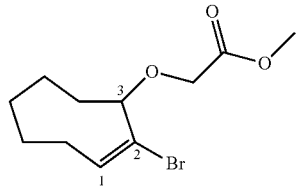

3.85 g of silver perchlorate (i.e., 18.6 mmol) are added to a solution of 8,8-diboromobicyclo[5.1.0]octane (2.5 g, i.e. 9.3 mmol) and methyl glycolate (6.35 ml, i.e. 83.9 mmol) dissolved in 5 ml of anhydrous toluene in a dry round-bottomed flask, under Ar and protected from the light by an aluminum film. The reaction mixture is stirred at ambient temperature for 1 h 30 and then the silver salts are filtered off on a sintered glass funnel and washed with AcOEt. The solution is concentrated under vacuum to give a brown viscous oil, which is purified by chromatography on silica gel (2-15% AcOEt in cyclohexane) in order to obtain the product in the form of a yellow oil with a w=1.6 g, i.e. 65% yield (litt. 22%[5]).

$R_f$(petroleum ether/AcOEt 5%)=0.25;

$^1$H NMR ($CDCl_3$, 200 MHz): δ (ppm) 0.7-2.2 (m, 8H); 2.28 (m, 1H); 2.70 (ddd, J=5, 11.5 and 23.5 Hz, 1H); 3.72 (s, 3H, OMe); 3.94 (d, $J_{9-9'}$=16.5 Hz, 1H, $H_9$); 4.10 (dd, $J_{3-4'}$=5 Hz, $J_{3-4'}$=10 Hz, 1H, $H_3$); 4.23 (d, $J_{9-9'}$=16.5 Hz, 1H, $H_{9'}$); 6.20 (dd, $J_{1-8'}$=4 Hz, $J_{1-8'}$=11.5 Hz, 1H, $H_1$);

$^{13}$C NMR ($CDCl_3$, 50 MHz): 26.2; 28.0; 33.4; 36.5; 39.3 ($C_{4-8}$); 51.8 ($C_3$); 65.4 ($C_{11}$); 84.8 ($C_9$); 131.4 ($C_2$ quat.); 133 ($C_1$); 170.7 ($C_{10}$ quat.);

Mass: $ESI^+$ m/z $[M+H]^+$=277.6 and 279.6; $[M+Na]^+$=299.6 and 301.6; $[2M+H]^+$=553.0, 555.0 and 557.0; $[2M+Na]$=575.0, 576.9 and 578.8;

IR: υ (cm$^{-1}$) 2931 υ$_{CH}$; 2856 υ$_{CH2}$; 1754 υ$_{C=O}$; 1445 υ$_{trans\ C=C}$; 1132 υ$_{ether\ COC}$.

3—Synthesis of cyclooct-1-yne-3-glycolic acid

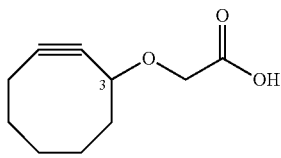 [SMILES: O=C(O)COC1C#CCCCCC1]

A 0.5M solution of sodium methoxide in methanol is added to 250 mg of methyl 2-bromocyclooctene-3-glycolate (i.e., 0.90 mmol). The mixture is stirred at temperature for 2 days.

The reaction mixture is acidified with 1M HCl and then extracted with AcOEt, drying is carried out over MgSO$_4$ and the solvents are then evaporated. The product is purified on silica gel with AcOEt and is obtained in the form of a yellow oil with a weight of 120 mg, i.e. 80% yield.

$^1$H NMR (CDCl$_3$, 200 MHz): δ (ppm) 1.3-2.3 (m, 10H); 4.45 (d, J$_{9-9'}$=17 Hz, 1H, H$_9$); 4.50 (m, 1H, H$_3$); 4.58 (d, J$_{9-9'}$=17 Hz, 1H, H$_{9'}$);

$^{13}$C NMR (CDCl$_3$, 50 MHz) δ (ppm)

Mass: ESI$^+$ m/z

4—Synthesis of the cyclooctyne-ferrocene of Formula I-A

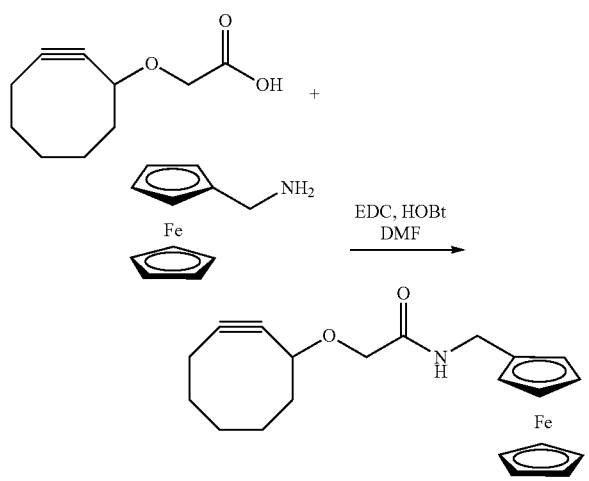

41 mg of EDC (i.e., 0.21 mmol) and 28 mg of HOBt (i.e., 0.21 mmol) are added to a solution of cyclooct-1-yne-3-glycolic acid (33 mg, i.e. 0.18 mmol) in 2 ml of anhydrous DMF. After stirring under argon at ambient temperature for 15 min, a solution of ferrocene-methylamine[9] (45 mg, i.e. 0.21 mmol) in 0.8 ml of anhydrous DMF is added dropwise. Stirring is maintained for 24 h.

After addition of 10 ml of water, the reaction mixture is extracted with dichloromethane. The organic phase is dried over anhydrous Na$_2$SO$_4$, filtered and concentrated under vacuum. The product is purified on silica gel (DCM/MeOH: 99/1) and is obtained in the form of a yellow oil (21 mg, i.e. 30% yield).

Redox Activity of the Compound of Formula I-A in Solution:

It was confirmed that this compound indeed has a redox activity in solution.

The cyclic voltammetry measurements were carried out using a system comprising three electrodes: the working electrode is a platinum electrode, the reference electrode is a saturated calomel electrode and the counterelectrode is a platinum electrode. The solution studied is a 2 mM solution of cyclooctyne-ferrocene in the electrolyte Bu$_4$NPF$_6$ (0.1M)/propylene carbonate.

An oxidation peak is identified at 0.5V and a reduction peak is identified at 0.35V. It is confirmed that the modification of the ferrocene by the cyclooctyne does not destroy its redox activity.

Grafting to Silicon Surface of a Compound of Formula I-A at Different Temperatures:

A silicon surface, hydrogenated beforehand by treatment with 1% HF, is introduced into a 1 mM solution of the alkyne under consideration (cyclooctyne-ferrocene or ferrocene-alkyne) in mesitylene. The reaction medium is heated (100° C./130° C./180° C.) under an argon atmosphere for 2 h. After cooling to ambient temperature, the surface is washed and subjected to ultrasound in dichloromethane and dried under argon.

At 180° C. (reference temperature):

The I-A compound gives an electrochemical signature, indicating that it is indeed grafted to the surface.

The drift of the baseline is slightly more pronounced than with the reference compound of formula I-E, which indicates that, in this case, a small amount of oxide has formed at the surface.

This is because there is always a competition between the grafting reaction and the reaction for the formation of oxide (due to the traces of oxygen and of water in the medium). The more reactive the compound to be grafted, the less this oxide is formed.

This first experiment shows that the compound of formula I-A has a greater reactivity, in comparison with the reference compound of formula I-E.

130° C.:

This temperature is generally too low for monosubstituted alkynes to react.

This is observed with regard to the reference ferrocene-alkyne, the redox activity of which is visible but very strongly masked by a strong oxidation of the substrate, indicating that the ferrocene has only partially reacted.

In contrast, the redox signature of the compound of formula I-A is much clearer and the oxidation of the surface rather reduced (comparable to that obtained at 180° C. with the reference compound of formula I-E).

100° C.:

No reactivity of the reference compound of formula I-E.

Very low reactivity of the compound of formula I-A, even if its exists. The oxidation of the surface is predominantly observed.

EXAMPLE 3

The disubstituted alkyne according to the invention used here is the alkyne cyclooct-1-yne-3-glycolic acid, as in example 2, and the ferrocene molecule has the following formula:

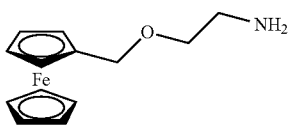

Cyclooct-1-yne-3-glycolic acid was obtained as in example 1.

41 mg of EDC (i.e., 0.21 mmol) and 28 mg of HOBt (i.e., 0.21 mmol) are then added to a solution of cyclo-oct-1-yne-3-glycolic acid (34 mg, i.e. 0.19 mmol) in 2 ml of anhydrous DMF. After stirring under argon at ambient temperature for 15 min, 2-aminoethyl ferrocenylmethyl ether (70 mg, i.e. 0.21 mmol) is added. Stirring is maintained for 24 h. After the evaporation of the solvent under vacuum, the residue is redissolved in dichloromethane. The organic phase is washed with water, dried over anhydrous $Na_2SO_4$, filtered and concentrated under vacuum. The product is purified on silica gel (DCM/MeOH: 98/2) and is obtained in the form of a yellow oil (31 mg, i.e. 39% yield).

The following compound of formula I-B is obtained:

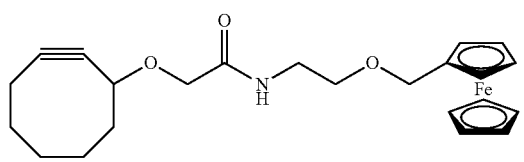

Redox Activity of the Compound of Formula I-B in Solution:

It was first confirmed that this compound indeed has a redox activity in solution.

For this, the compound of formula I-B was dissolved and its redox activity was tested by cyclic voltammetry using a system comprising three electrodes. The working electrode is a platinum electrode, the reference electrode is a saturated calomel electrode and the counterelectrode is a platinum electrode. The electrode used is a 1M solution of $Bu_4NPF_6$ in propylene carbonate. The cyclic voltammetry measurement was carried out at a scan rate of 500 mV/s.

An oxidation peak is identified at 0.448 V and a reduction peak is identified at 0.317 V. It is thus confirmed that the modification of the ferrocene by the cyclooctyne does not destroy the redox activity of the ferrocene.

Grafting to silicon surface of the compound of formula I-B at different temperatures:

A silicon surface, hydrogenated beforehand by treatment with 1% HF, is introduced into a 1 mM solution of compound of formula I-B in mesitylene. The reaction medium is heated (100° C./130° C./180° C.) under an argon atmosphere for 2 h. After cooling at ambient temperature, the surface is washed and subjected to ultrasound in dichloromethane and dried under argon.

In the case of the compound I-B, the spacer arm between the cyclooctyne and the redox (ferrocene) molecule is longer. This factor makes possible more efficient grafting (by reducing the steric trouble) as the grafting is effective from 100° C. However, at this temperature, the grafting appears, however, to be less efficient since a greater reoxidation of the substrate is observed (greater ΔE(ox/red)). On the other hand, from 130° C., the results show (both from the viewpoint of the ΔE(ox/red) values and of the grafting density) that the grafting is very successful. In that case, it is thus apparent that there is a sufficient thermal activation to allow the grafting and that there is a better arrangement of the layer formed due to the longer spacer arm, which is accompanied by a lower reoxidation of the substrate.

It is seen, from examples 2 and 3, that the cyclic alkyne makes possible the grafting of the group of interest, in this instance a ferrocene group, to an Si—H surface at temperatures which are lower than that generally used (180° C.) with the monosubstituted alkynes used in the prior art.

EXAMPLE 4

The disubstituted alkyne according to the invention used here is the butynoic acid of following formula:

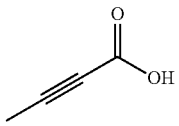

and the ferrocene molecule has the following formula:

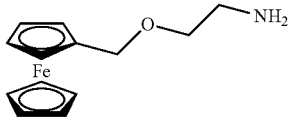

78 mg of EDC (i.e., 0.41 mmol) and 57 mg of HOBt (i.e., 0.42 mmol) are added to a solution of the butynoic acid (30 mg, i.e. 0.36 mmol) in 2 ml of anhydrous DMF. After stirring under argon at ambient temperature for 15 min, 2-aminoethyl ferrocenylmethyl ether (102 mg, i.e. 0.40 mmol) is added. Stirring is maintained for 24 h.

After evaporating the solvent under vacuum, the residue is redissolved in dichloromethane. The organic phase is washed with water, dried over anhydrous $Na_2SO_4$, filtered and concentrated under vacuum. The product is purified on silica gel (DCM/MeOH: 95/5) and is obtained in the form of a yellow oil (30 mg, i.e. 26% yield).

The compound of following formula I-C is obtained:

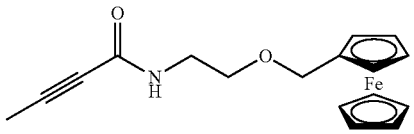

Redox Activity of this Molecule in Solution:

It was confirmed that this compound indeed has a redox activity in solution.

The compound of formula I-C was dissolved and its redox activity was tested by cyclic voltammetry using a system comprising three electrodes. The working electrode is a platinum electrode, the reference electrode is a saturated calomel electrode and the counterelectrode is a platinum electrode. The electrolyte used is a 1M solution of $Bu_4NPF_6$ in propylene carbonate. The cyclic voltammetry measurement was carried out at a scan rate of 500 mV/s.

An oxidation peak at 0.494 V is identified and a reduction peak at 0.345 V is identified. It is thus confirmed that the modification of the ferrocene by the disubstituted alkyne does not destroy the redox activity of the ferrocene.

Grafting to Silicon Surface at Different Temperatures:

A silicon surface, hydrogenated beforehand by treatment with 1% HF, is introduced into a 1 mM solution of compound of formula I-C in mesitylene. The reaction medium is heated (100° C./130° C./180° C.) under an argon atmosphere for 2 h. After cooling at ambient temperature, the surface is washed and subjected to ultrasound in dichloromethane and dried under argon.

In the case of the compound I-C, the grafting to Si—H is effective from 100° C. For the grafting operations carried out at 100° C. and 130° C., the difference in potential between the oxidation and the reduction ($\Delta E(ox/red)$) is low (of the order of 100 mV).

EXAMPLE 5

The disubstituted alkyne according to the invention used here is 9-undecynoic acid of following formula:

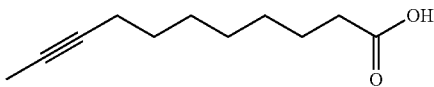

and the molecule of interest is the same ferrocene molecule as that used in example 3.

The operation was carried out in the following way:

127 mg of EDC (i.e., 0.66 mmol) and 90 mg of HOBt (i.e., 0.67 mmol) are added to a solution of 9-undecynoic acid (107 mg, i.e. 0.59 mmol) in 5 ml of anhydrous DMF. After stirring under argon at ambient temperature for 15 min, 2-aminoethyl ferrocenylmethyl ether (171 mg, i.e. 0.66 mmol) is added. Stirring is maintained for 24 h. After evaporating the solvent under vacuum, the residue is redissolved in dichloro-methane. The organic phase is washed with water, dried over anhydrous $Na_2SO_4$, filtered and concentrated under vacuum. The product is purified on silica gel (DCM/MeOH: 98/2) and is obtained in the form of an orange oil (175 mg, i.e. 70% yield).

The compound obtained is the compound of following formula I-D:

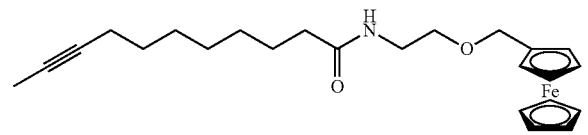

Redox Activity of this Compound in Solution:

It was confirmed that this molecule indeed has a redox activity in solution.

The compound of formula I-D was dissolved and its redox activity was tested by cyclic voltammetry using a system comprising three electrodes. The working electrode is a platinum electrode, the reference electrode is a saturated calomel electrode and the counter electrode is a platinum electrode. The electrolyte used is a 1M solution of $Bu_4NPF_6$ in propylene carbonate. The cyclic voltammetry measurement was carried out at a scan rate of 500 mV/s.

An oxidation peak at 0.463 V is identified and a reduction peak at 0.292 V is identified. It is thus confirmed that the modification of the ferrocene by the disubstituted alkyne does not destroy the redox activity of the ferrocene.

Grafting to Silicon Surface at Different Temperatures:

A silicon surface, hydrogenated beforehand by treatment with 1% HF, is introduced into a 1 mM solution of compound of formula I-D in mesitylene. The reaction medium is heated (100° C./130° C./180° C.) under an argon atmosphere for 2 h. After cooling at ambient temperature, the surface is washed and subjected to ultrasound in dichloromethane and dried under argon.

In the case of the compound I-D, the grafting is effective from 100° C. However, the grafting is more effective when it is carried out at 180° C., where a low $\Delta E(ox/red)$, that is to say an absence of reoxidation of the substrate, is observed.

The grafting operations carried out at 100° C. and at 130° C. are, in comparison with the compound I-C, much less efficient. This difference is explained by an absence of activation in the α position of the compound I-D, in comparison with the compound I-C, where the electron-withdrawing amide functional group makes it possible to increase the reactivity of the alkyne.

The invention claimed is:

1. A process for functionalizing a surface of a substrate made of a semiconducting material, the process comprising:

a) reacting a reactive group F1 of a compound of formula I:

with a reactive group of F2 of a molecule of formula II:

and b) reacting a triple bond of the compound of formula I with a semiconducting material, wherein A is selected from:

1) an alkyne of formula:

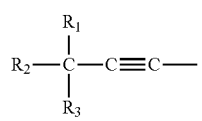

,wherein $R_1$, $R_2$, and $R_3$ are each independently a hydrogen atom; a halogen atom; an —OH group; an —$NH_2$ group; an —SH group; a saturated, linear or branched, $C_1$ to $C_{30}$ alkyl chain which optionally comprises at least one selected from the group consisting of a heteroatom, an aryl group, an amine group, an ester group, a hydroxylamine group, an oxime group, and an amide group; and is optionally substituted by at least one halogen atom; and 2) an 8- to 12-membered cycloalkyne or heterocycloalkyne which is optionally substituted by the $R_1$ group, E1 is a saturated or unsaturated, linear or branched, $C_1$ to $C_{30}$ alkyl chain which optionally comprises at least one selected from the group consisting of a heteroatom, an aryl group, an amine group, an ester group, a hydroxylamine group, an oxime group, and an amide group, or is optionally substituted by at least one halogen atom, n1 is 0 or 1, F2 is a reactive group reacting with the reactive group F1, wherein E2 is a saturated or unsaturated, linear or branched, $C_1$ to $C_{30}$ alkyl chain which optionally comprises at least one selected from the group consisting of a heteroatom, an aryl group, an amine group, an ester group, a hydroxylamine group, an oxime group, and an amide group, or is optionally substituted by at least one halogen atom, n2 is 0 or 1, and X is selected from the group consisting of a porphyrin molecule, an anthracene molecule, a naphthalene molecule, a fullerene molecule, a polyoxometalate molecule, and a ferrocene group.

2. The process as claimed in claim 1, wherein b) is carried out before a).

3. The process as claimed in claim 2, further comprising:
protecting the reactive group F1, before a), and
deprotecting the reactive group F1, before b).

4. The process as claimed in claim 1, wherein a) is carried out before b).

5. The process as claimed in claim 1,
wherein the semiconducting material of the substrate is at least one selected from the group consisting of silicon, germanium, a silicon alloy, and a germanium alloy.

6. The process as claimed in claim 1,
wherein $R_1$, $R_2$ and $R_3$, when present, are each independently a hydrogen atom; a halogen atom, and a saturated, linear or branched, $C_1$ to $C_{30}$ alkyl chain which optionally comprises at least one selected from the group consisting of a heteroatom, an aryl group, an amine group, and is optionally substituted by at least one halogen atom.

7. The process as claimed in claim 1,
wherein $R_2$ and $R_3$ are H and
$R_1$ is a linear or branched $C_1$ to $C_5$ alkyl chain which optionally comprises a heteroatom.

8. The process as claimed in claim 1,
wherein E1 is a saturated, linear or branched, $C_1$ to $C_5$ alkyl which optionally comprises a heteroatom.

9. The process as claimed in claim 1,
wherein F1 and F2 are selected from the group consisting of a carboxyl group, a radical entity, a hydroxyl group, an alcohol group, an amine group, an ester group, an aldehyde group, a hydrazide group, a ketone group, an epoxy group, an isocyanate group, a maleimide group, a thiol group, and a hydroxylamine group.

10. The process as claimed in claim 1,
wherein
$R_1$, $R_2$, and $R_3$, when present, are H,
n1 is 0,
F1 is a —COOH radical, and
F2 is an —$NH_2$ radical.

11. The process as claimed in claim 1,
wherein
$R_1$ $R_2$ and $R_3$, when present, are H,
n1 is 1,
E1 is a —$C_6H_{12}$— chain,
F1 is a —COOH radical, and
F2 is an —$NH_2$ radical.

12. The process as claimed in claim 1,
wherein
A is an unsubstituted cyclooctyne,
n1 is 1,
E1 is an —O—$CH_2$— chain,
F1 is a —COOH radical, and
F2 is an —$NH_2$ radical.

13. The process as claimed in claim 1,
wherein E2 is a —$(CH_2)_2$—O—$CH_2$— chain.

14. The process as claimed in claim 1,
wherein X is a ferrocene group.

15. The process as claimed in claim 1,
wherein A is an unsubstituted cyclooctyne.

* * * * *